United States Patent [19]

Esteve Bianchini et al.

[11] 4,193,918
[45] Mar. 18, 1980

[54] PROCESS FOR THE PREPARATION OF HYDROXY-ALPHA-AMINO-BENZYL PENICILLIN

[75] Inventors: Asunción Esteve Bianchini; Antonio L. Palomo Coll, both of Barcelona, Spain

[73] Assignee: Antibioticos, Madrid, Spain

[21] Appl. No.: 911,513

[22] Filed: Jun. 1, 1978

[30] Foreign Application Priority Data

Jun. 4, 1977 [ES] Spain ................................ 459.494

[51] Int. Cl.$^2$ .......................................... C07D 499/68
[52] U.S. Cl. ................................................. 260/239.1
[58] Field of Search ..................................... 260/239.1

[56] References Cited

U.S. PATENT DOCUMENTS

| | | |
|---|---|---|
| 3,971,775 | 7/1976 | Cowley et al. ............... 260/239.1 |
| 3,980,637 | 9/1976 | Grossman et al. ............ 260/239.1 |
| 4,128,547 | 12/1978 | Van der Drift et al. ........ 260/239.1 |

OTHER PUBLICATIONS

Gupta: Synthesis, 724 (1975).

*Primary Examiner*—Bernard Helfin
*Assistant Examiner*—Vera C. Clarke
*Attorney, Agent, or Firm*—Haseltine, Lake & Waters

[57] ABSTRACT

A novel process for the preparation of hydroxy-alpha-amino-benzyl penicillin, particularly the p-hydroxy derivative known as amoxicillin.

5 Claims, No Drawings

PROCESS FOR THE PREPARATION OF HYDROXY-ALPHA-AMINO-BENZYL PENICILLIN

FIELD OF THE INVENTION

This invention relates to a novel process for the preparation of hydroxy-alpha-aminobenzyl penicillins, particularly the p-hydroxy derivative known as amoxicillin, an antibiotic of interest in human and veterinary medicine.

DESCRIPTION OF THE PRIOR ART

The processes described in the technical literature use p-hydroxy-C-phenylglycine with a protected amino group, preferably as enamine and convert these sodium or potassium salts into mixed anhydrides by the classical methods of pivalyl chloride or alkyl chloroformates, such as ethyl chloroformate. The use of the aminoacid hydrochloride chloride has also been suggested. These compounds are then reacted with 6-aminopenicillanic acid (6-APA).

These methods have disadvantages reflected in the yield and purity of the antibiotic, due to the presence of the free hydroxyl function, causing undesirable side reactions and to the use of pyridine bases which are hard to eliminate and which contaminate the antibiotic. The insolubility of the p-hydroxy-C-phenylglycine derivatives in organic solvents, particularly of the enamine salts in methylene chloride, hinder the reaction and consequently cause low conversion yields. It is also known that 1,3-oxazolidin-5-ones are formed with a yield of 70–90%, when operating at −20°, in the preparation of p-hydroxy-C-phenylglycine enamine salt alkyloxyformic anhydrides. (Gupta; Synthesis, 724, 1975). Thus, not only are low amoxicillin yields obtained, a maximum of 90% by weight being attained with respect to the 6-aminopenicillanic acid (6-APA), but also, with the use of pyridine compounds, the antibiotic is contaminated. It is known that a p-hydroxy-C-phenylglycine enamine potassium salt, derived from ethyl or methyl acetylacetate, is insoluble in methylene chloride and other organic solvents, whereby the formation of the anhydride proceeds with difficulty and low yields, giving rise to undesirable conversions with participation of the hydroxyl function. Likewise, the literature contains references that pyrrole derivatives are produced with trifluoracetic anhydride (Gupta; Synthesis, 726, 1975).

SUMMARY OF THE INVENTION

It has now been discovered that the protection of the phenolic hydroxyl and the formation of salts soluble in methylene chloride is an important, fundamental fact in the amoxicillin preparation process technology, so as to attain better yields and high purity levels; that is, it has been possible to prepare the compound of the following formula I,

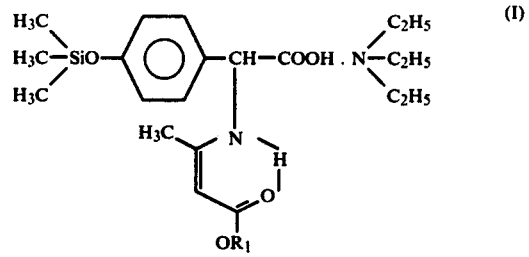

wherein $R_1$ is a methyl or ethyl radical. This compound, with pivalyl chloride, 2-ethylhexanoyl chloride or an alkyl chloroformate having from one to seven carbon atoms, forms the corresponding mixed anhydride and thereafter, on treatment with a triethylamine salt (TEA) or 6-APA trimethylsilyl ester, produces an intermediate which gives the antibiotic by hydrolysis.

Thus, the object of the invention is to provide a process wherein the conversion product resulting from D(−)p-hydroxy-C-phenylglycine with ethyl or methyl acetylacetate and triethylamine is made to react with 3-trimethylsilyl-2-oxazolidinone to obtain a compound of formula I which is reacted with a compound selected from the group formed by pivalyl chloride, 2-ethylhexanoyl chloride and alkyl chloroformate to obtain a compound of the general formula II

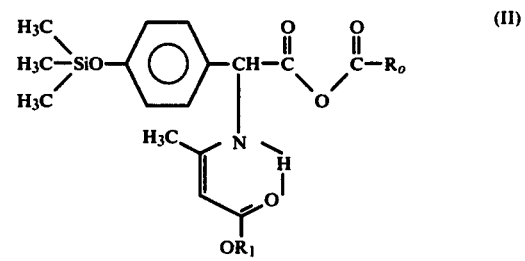

wherein $R_1$ has the meaning given hereinbefore and $R_o$ may be a low molecular weight alkoxy group or an alkyl group having from four to nine carbon atoms and which, thereafter, is reacted with a triethylamine salt or, preferably, with the trimethylsilyl ester of 6-aminopenicillanic acid to obtain an intermediate compound of the following formula III

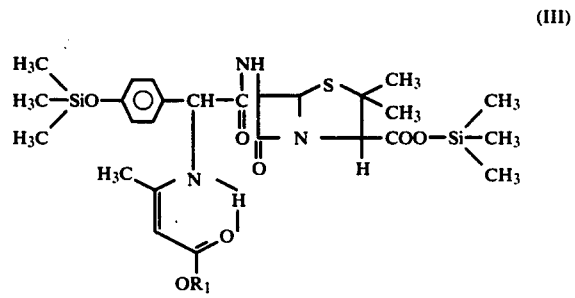

wherein $R_1$ has the meaning given hereinbefore and which with the addition of water and acidulation to pH=0.6 gives a solution of amoxicillin from which the antibiotic is isolated by precipitation at pH=3.30 to 4.20.

The new intermediate compounds of the process and the compound corresponding to formula I are prepared, as shown in the following scheme, either by sequence (a) or by sequence (b) wherein R is the enamine structural fraction, for example, derived from ethyl or methyl acetylacetate and $R_1$ is a methyl or ethyl radical.

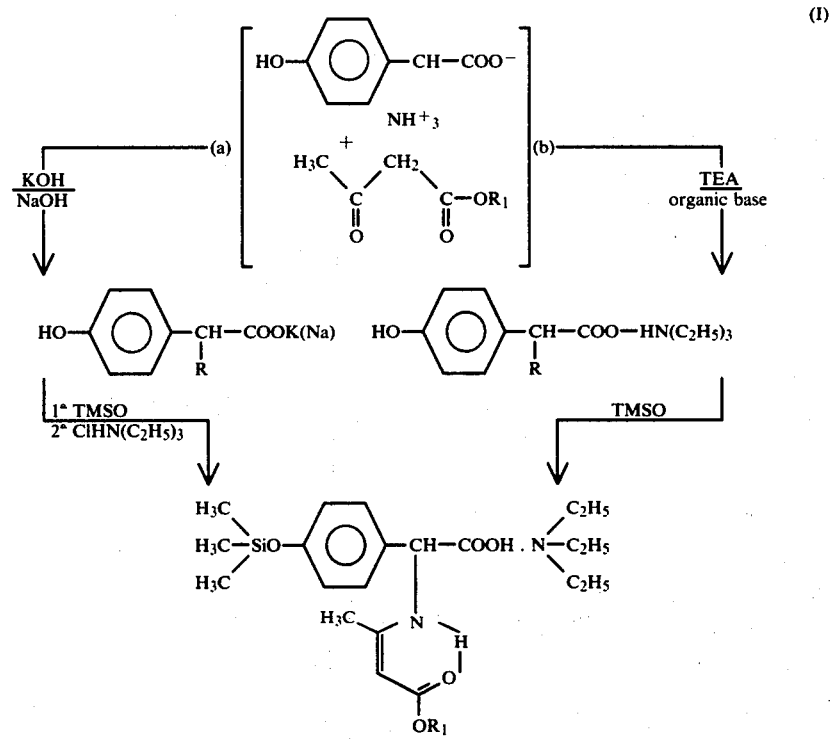

(I)

In accordance with sequence (a), the prior treatment of the sodium or potassium salt with a 3-trialkylsilyl-2-oxazolidinone, for example 3-trimethylsilyl-2-oxazolidinone (TMSO) affords protection for the phenolic hydroxyl derivative in the form of a trimethylsilyloxy derivative, which behaves suitably in methylene chloride. It is thereafter reacted with a triethylamine hydrochloride equivalent to produce a solution of the compound of formula I. The preparation of other organic base salts, such as N-ethylmorpholine and N-methylpiperidine, is similar. In sequence (b), the intermediate triethylamine salt is prepared by heating the alcoholic solution, for example, ethanol, methanol, or isopropanol, of ethyl or methyl acetylacetate with p-hydroxy-C-phenylglycine. After evaporating the solvent at reduced pressure and dissolving the residue in methylene chloride in the presence of TMSO, the product of formula I is obtained. The N-methylmorpholine and N-ethylpiperidine salts are prepared in a similar way.

Several silylating reagents are known in the silylating techniques, nevertheless, they have turned out to be inoperative for correct protection of the phenolic hydroxyl and have shown themselves to be unspecific or produce by-products which interfere in the mixed anhydride formation reaction. Thus, trimethylchlorosilane causes a blockage of the carboxyl function and alteration of the enamine together with mixtures of the acid and free hydroxyl present in the reaction medium; hexamethyldisilazane produces ammonia; trimethylsilyldiethylamine forms diethylamine; BSA (bistrimethylsilylacetamide) releases silylacetamide; trimethylsilylimidazole releases imidazole; all of which are incompatible with the mixed anhydride preparation reagents. On the contrary, TMSO has shown itself to be specific for the preparation of the compound of formula I and the reaction by-product, 2-oxazolidone, is an inert, non-toxic compound easily eliminable as a result of being water soluble.

A further surprising result has been found when reacting one equivalent of each of p-hydroxy-C-phenylglycine, triethylamine and ethyl acetylacetate in methanol and operating in a similar way to the methods already described which use sodium or potassium hydroxide. This reaction proved to be impracticable and produced decomposition products instead of the desired compound, whereas this latter was easily achieved when two equivalents of tertiary organic base were used, with no decomposition occurring.

In the sequence of the process, the reaction of the product of formula I with an acid chloride, preferably pivalyl chloride or a low molecular weight alkyl chloroformate, such as ethyl chloroformate, forms the mixed anhydride, where the participation of the hydroxyl is not possible, since it has been previously blocked. As well as the N-silyl derivatives described e.g. in Spanish Pat. No. 411.867, Austrian Pat. No. 327.223, U.S. Pat. No. 3,947,465, French Pat. No. 74.05700, British Pat. No. 1.411.725, also appropriate for the purposes of the present invention are N-tert. butyldimethylsilyl-2-oxazolidinone and N-triisopropylsilyl-2-oxazolidinone prepared in exactly the same way as the process described in the above patents. According to the hydrocarbonated nature of the groups bonded to the silicon atom, they offer a more intensive protection so that the formula I compounds having tert. butyldimethylsililoxy and triisopropylsilyloxy groups instead of trimethylsilyloxy are not altered by the presence of water and must be split off by the presence of inorganic acids, preferably hydrochloric acid.

The effect of the acid hydrolysis is seen in the simultaneous elimination of both protector groups, hydroxyl and amino function, or the alternative splitting off first of a large portion of the enamine group, followed by release of the hydroxyl group. On the other hand, the carboxyl function blocked by trimethylsilyl ester is rapidly released by the simple action of water. One practical way of performing all the releases is to add an acid aqueous solution so that the medium reaches a pH of from 0.55 to 0.65 and amoxicillin is precipitated out of the water phase at pH=3.30–4.20. In the case of the chlorodimethylsilyloxy protector group, the addition of water is sufficient to reach the optimum hydrolysis pH and the amino function is released as well as the hydroxyl function.

EXAMPLE 1

A suspension of D(−) p-hydroxy-N(1-ethoxycarbonyl-2-propenyl)-alpha-aminophenylacetic acid potassium salt (15.10 g; 4.76 cmole) in methylene chloride (30 ml), dimethylacetamide (7.5 ml) and 3-trimethylsilyl-2-oxazolidinone (TMSO) (7.5 ml) was stirred for 40 minutes at 20°–25° C., to provide a pale coloured, fluid mass. This was chilled to −20° C., pivalyl chloride (5.74 g) in methylene chloride (5 ml) was added at one time and the reaction temperature was held at −10° to −7° C. for 60 minutes. A solution of 6-aminopenicillanic acid (6-APA) (8.650 g; 4 cmoles), methylene chloride (80 ml), triethylamine (TEA) (0.5 ml) and TMSO (20 ml) was added gradually over a period of 30 minutes at a temperature of −32° C. to the translucid mass formed above. Thereafter the mixture was held at the same temperature for 90 minutes, with stirring. Then water was added (50 ml) and concentrated hydrochloric acid at one time, with stirring at a temperature of 0 to 5° C. and the pH adjusted to 0.55–0.65. After from 45 to 60 minutes, the water phase was drawn off, its pH was adjusted to 4.16 with ammonia solution and isopropanol (20 ml) was added to precipitate out amoxicillin. After stirring for 60 minutes at 5° C., the amoxicillin was isolated by filtration, washed and dried. The yield was 14.70 g of antibiotic (ratio 1:1.70 with respect to 6-APA).

EXAMPLE 2

A suspension of the potassium salt of D(−) p-hydroxy-N(1-methoxycarbonyl-2-propenyl)-alpha-aminophenylacetic acid (3.607 g, 1.19 cmoles), methylene chloride (25 ml), dimethylacetamide (2.5 ml) and TMSO (1.82 ml) was stirred at room temperature (20-25° C.) for 45 minutes. Thereafter triethylamine hydrochloride (1.63 g; 1.19 cmoles) was added and after 15 minutes the result was a translucid solution which was cooled to −20° C. Pivalyl chloride (1.45 ml; 1.2 cmoles) in methylene chloride (1.25 ml) and a drop of triethylamine were added. The reaction mixture was stirred for 60 minutes at a temperature of from −10 to −7° C. Thereafter a solution of 6-APA (1 cmole) prepared according to Example 1 was added under the conditions specified in that Example. Then, in a like manner, 3.25 g of amoxicillin (ratio of 1:1,50 with respect to 6-APA) were obtained.

EXAMPLE 3

Following Example 2 and replacing the methoxycarbonyl derivative by the corresponding ethoxycarbonyl derivative (3.77 g; 1.19 cmoles) and the solution of the 6-APA trimethylsilyl ester by the 6-APA triethylamine salt (prepared in the usual way), the result is amoxicillin with identical yield.

EXAMPLE 4

Following Example 1, there was added first in the silylation stage TMSO (7.0 ml) and then triethylamine hydrochloride (6.52 g; 4.76 cmole), the pivalyl chloride being replaced thereafter by ethyl chloroformate (5.38 ml; 4.6 cmoles), the temperature being held at −10° C. for 30 minutes. Then TMSO (7.30 ml) was added. The mixture was cooled to −35° C. and by operating in the same way, amoxicillin was obtained (12.11 g) (ratio 1:1.40 with respect to 6-APA).

EXAMPLE 5

Following Example 4 and replacing the ethyl chloroformate by 2-ethylhexanoyl chloride, amoxicillin was isolated (11.26 g), ratio 1:1.45 with respect to 6-APA.

EXAMPLE 6

A suspension of D(−) p-hydroxy-C-phenylglycine (3.34 g; 2 cmoles) in 99.5% ethanol (50 ml), triethylamine (5.44 ml; 4 cmoles) and ethyl acetylacetate (4.28 g; 4 cmoles) was heated with stirring to gentle reflux to give a complete solution in 60 minutes. Thereafter the solvent and excess TEA was evaporated off at reduced pressure and the residual oil (9.4 g) was dissolved in methylene chloride (20 ml) containing TMSO (3.0 ml), with stirring for 30 minutes at room temperature. Thereafter the mixture was chilled to −15° C. and pivalyl chloride (2.4 ml; 2 cmoles) in methylene chloride (2.5 ml) and a drop of triethylamine solution were added in one operation and the mixture was allowed to rise to −10 to −8° C. with stirring for 45 minutes. The mixture was then cooled to −30° C. and a solution of 6-APA trimethylsilyl ester (2 cmoles) prepared according to Example 1 was gradually poured in. Thereafter the reaction mixture was treated as per Example 1 and amoxicillin was isolated (6.90 g); ratio 1:1.60 with respect to 6-APA.

EXAMPLE 7

Following the previous Example and replacing the ethanol by methanol and the triethylamine by N-methylmorpholine, amoxicillin is produced with a similar yield.

EXAMPLE 8

A suspension of the potassium salt of D(−) p-hydroxy-N(1-ethoxycarbonyl-2-propenyl)-alpha-aminophenyl acetic acid (6.342 g; 2.0 cmoles) in methylene chloride (25 ml), dimethylformamide (3 ml) and N-triisopropylsilyl-2-oxazolidinone (4.80 g; 2 cmoles) was stirred for 60 minutes at a temperature of 35° C. Thereafter, triethylamine hydrochloride (3.26 g; 2.38 cmoles) was added to give a solution which was cooled to −15° C. and thereafter treated as in Example 1. Amoxicillin was isolated with a similar yield.

EXAMPLE 9

Following the previous Example and replacing the N-triisopropylsilyl-2-oxazolidinone by N-tert. butyldimethylsilyl-2-oxazolidinone (4.10 g; 2 cmoles), amoxicillin was isolated with a similar yield.

EXAMPLE 10

A suspension of D(−) p-hydroxyphenylglycine (6.88 g; 4 cmoles) in ethanol (75 ml) with ethyl acetylacetate (8.56 g; 8 cmoles) and N-ethylpiperidine (11.0 g; 8 cmoles) was heated to gentle reflux with stirring to give a solution which, after 1.5 hours, was cooled in a water-ice bath and the crystals formed were isolated by filtration. After washing with isopropanol and drying, they gave 12.8 g of the N-ethylpiperidine salt of D(−) p-hydroxy-N(1-ethoxycarbonyl-2-propenyl)-alpha-aminophenyl acetic acid, in acicular prisms, with m.p.=142–144° C. (d) and $[\alpha]_D^{20}=97.5°$ C. (c=4% in $H_2O$; in time the optical activity diminishes: $[\alpha]_D^{20}=-68$ to $-70°$ (c=1% in HCl 1N).

When the foregoing process was followed with methanol instead of ethanol, the result was a solution in 30 minutes; the solvent was evaporated off at reduced pressure; isopropanol (50 ml) was added to produce a microcrystalline precipitation which, after 120 minutes in a water-ice bath, was filtered, washed with isopropanol and dried to give the identical compound, with a yield of 92.5% to 96% of theory.

TMSO (3.0 ml) was added to a suspension of this N-ethylpiperidine salt (8.3 g; 2.2 cmoles) in methylene chloride (15 ml) and dimethylformamide (3.75 ml) to give a solution which was stirred for 60 minutes at room temperature. It was chilled to −15° and a solution of pivalyl chloride (2.66 ml; 2.2 cmoles) in methylene chloride (2.5 ml) and N-methylmorpholine (0.1 ml) was added at one go. The solution was allowed to rise to a temperature of from −10 to −7° C. and stirred for 60 minutes. Thereafter it was cooled to −32° C. and a further solution of 6-APA (4.325 g; 2 cmoles) prepared as described in Example 1 was added over a period of 30 minutes. After 90 minutes reaction, water (25 ml) and concentrated HCl to pH=0.67 were added and the mixture was stirred for 30 minutes. The water phase is drawn off, adjusted to pH=3.6 with ammonia to precipitate amoxicillin and finally is adjusted to pH=4.16–4.20. After 60 minutes stirring at 0–5° C., the solid is filtered, washed with isopropanol-water and thereafter with acetone to yield the antibiotic (7.0 g); ratio 1:1.6 with respect to 6-APA.

What we claim is:

1. Process for the preparation of hydroxy-alpha-amino-benzyl penicillin, characterized in that the conversion product of D(−) p-hydroxy-C-phenylglycine, ethyl or methyl acetylacetate and triethylamine is made to react with 3-trimethylsilyl-2-oxazolidinone to obtain the compound of the following formula I:

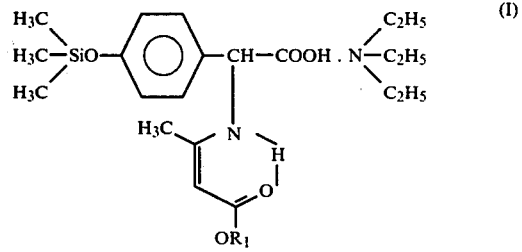

where $R_1$ is a methyl or ethyl radical, which compound is reacted with a compound selected from the group comprising pivalyl chloride, 2-ethylhexanoyl chloride and alkyl chloroformate to obtain a compound of the following formula II

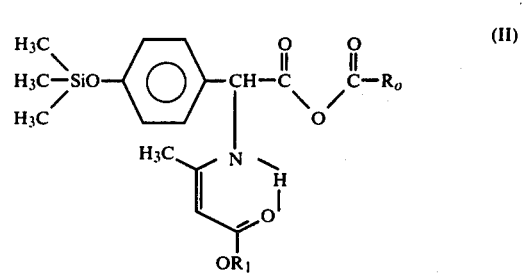

where $R_1$ has the meaning given hereinbefore and $R_o$ may be a low molecular weight alkoxy group or an alkyl group having from four to nine carbon atoms and which is thereafter reacted with a compound selected from the group consisting of the triethylamine salt and the trimethylsilyl ester of 6-aminopenicillanic acid, to obtain an intermediate of the following formula III

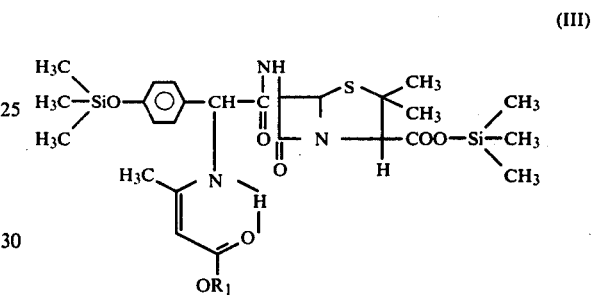

where $R_1$ has the meaning given hereinbefore, which, with the addition of water and acidulation to pH=0.6 gives a solution of amoxicillin, from which the antibiotic is isolated by precipitation at pH=3.30 to 4.20.

2. The process of claim 1, characterised in that the conversion product of D(−) p-hydroxy-C-phenylglycine, ethyl acetylacetate and sodium or potassium hydroxide is made to react first with trimethylsilyl-2-oxazolidinone and then with triethylamine hydrochloride to obtain a compound of formula I which is made to react with an acid chloride or chloroformate to form a compound of formula II which is thereafter made to react with a solution of 6-aminopenicillanic acid in the triethylamine salt or trimethylsilyl ester form in methylene chloride to produce a compound of formula III, which is treated with water and acid and from which amoxicillin is isolated on adjusting to pH=3.30 to 4.20.

3. The process of claim 1, characterised in that the conversion product of D(−) p-hydroxy-C-phenylglycine, ethyl acetylacetate and sodium or potassium hydroxide is made to react first with 3-trimethylsilyl-2-oxazolidinone and then with an acid chloride or alkyl chloroformate to obtain a compound of formula II, which is made to react with a solution of 6-aminopenicillanic acid in the form of its triethylamine salt or trimethylsilyl ester in methylene chloride to produce a compound of formula III, from which, with water and acid treatment and adjustment to pH=3.30 to 4.20, amoxicillin is isolated.

4. The process of claim 1, characterized in that a N-trialkylsilyl-2-oxazolidinone is used in the form of tert. butyldimethylsilyl-2-oxazolidinone or triisopropylsilyl-2-oxazolidinone, to obtain the corresponding derived compound of formula I, which is made to react first with an acid chloride or an alkyl chloroformate and the resulting product is combined with a solution of 6-aminopenicillanic acid in the form of its triethylamine salt or trimethylsilyl ester which is thereafter subjected to hydrolysis and from which amoxicillin is isolated by adjustment of the water phase to a pH of between 3.30 and 4.20.

5. The process of claim 1, characterised in that an N-alkylsilyl-2-oxazolidinone is made to react with the enamine of D(—) p-hydroxy-C-phenylglycine as salt of a tertiary organic base of up to eight carbon atoms and the conversion product in mixed anhydride is made to react thereafter with a solution of chlorodimethylsilyl-carboxy derivative of 6-aminopenicillanic acid to obtain amoxicillin.

* * * * *